(12) United States Patent
Haronian et al.

(10) Patent No.: US 6,465,241 B2
(45) Date of Patent: Oct. 15, 2002

(54) METHOD, CHIP, DEVICE AND SYSTEM FOR EFFECTING AND MONITORING NUCLEIC ACID ACCUMULATION

(75) Inventors: Dan Haronian, Efrat; Menachem Nathan, Tel Aviv; Jonathan M. Gershoni; Arieh Yaron, both of Rehovot, all of (IL)

(73) Assignee: Ramot University Authority for Applied Research and Industrial Development Ltd., Tel Aviv (IL)

(*) Notice: Subject to any disclaimer, the term of this patent is extended or adjusted under 35 U.S.C. 154(b) by 0 days.

(21) Appl. No.: 09/735,799

(22) Filed: Dec. 14, 2000

(65) Prior Publication Data

US 2002/0061519 A1 May 23, 2002

Related U.S. Application Data

(63) Continuation of application No. 09/157,531, filed on Sep. 21, 1998, now abandoned.

(51) Int. Cl.[7] .............................. C12M 1/34; C12Q 1/68; C12P 19/34; G01N 21/29; G01N 21/64
(52) U.S. Cl. ..................... 435/287.2; 435/6; 435/91.1; 435/287.1; 422/82.05; 422/82.11
(58) Field of Search ........................... 435/6, 91.1, 183, 435/283.1, 287.1, 287.2; 436/94; 536/23.1, 24.3, 24.33, 25.3, 25.32; 422/50, 55, 68.1, 82.05, 82.09, 82.11

(56) References Cited

U.S. PATENT DOCUMENTS

| | | |
|---|---|---|
| 5,485,277 A | 1/1996 | Foster |
| 5,498,392 A | 3/1996 | Wilding et al. |
| 5,599,668 A | 2/1997 | Stimpson et al. |
| 5,641,658 A | 6/1997 | Adams et al. |
| 5,737,457 A | 4/1998 | Saini et al. |

FOREIGN PATENT DOCUMENTS

| | | | |
|---|---|---|---|
| EP | 0517516 A1 | * | 9/1992 |
| WO | WO 97/27328 | * | 7/1907 |

OTHER PUBLICATIONS

Schneider et al., Hartman interomer: versatile integrated optic sensor for label–free, real–time quantification of nucleic acids, proteins, and pathogens. Clin. Chem., 43, 1757–1763, 1997.*

Karymov et al., Fixation of DNA directly on optical waveguide surfaces for molecular probe biosensor development. Sensors and Actuators B, 29, 324–327, 1995.*

Kruchinin et al., Surface plasma resonance monitoring by means of polarization state measurement in reflected light as the basis of a DNA–probe biosensor. Sensors and Actuators B, 30, 77–80, 1996.*

Lee etal, "Allelic Discrimination by Nick–Translation PCR with Fluorogenic Probes", *Nucleic Acid Research*, 2(16):3761–3766, 1993.

(List continued on next page.)

*Primary Examiner*—Ethan C. Whisenant
*Assistant Examiner*—Frank W Lu
(74) *Attorney, Agent, or Firm*—Mark M. Friedman (57) ABSTRACT

A nucleic acid accumulation analyzing chip comprising an optical waveguide having a radiation input port and a radiation output port, the optical waveguide being formed with at least one optical microcavity along its optical path, at least one oligonucleotide being immobilized to the optical waveguide in the microcavity, such that when the at least one oligonucleotide is contacted with reaction reagents under conditions allowing a nucleic acid accumulation reaction to take place, accumulated nucleic acid is detectable by providing radiation at the radiation input port of the optical waveguide and monitoring radiation signal modulation at the radiation output port of the optical waveguide.

12 Claims, 4 Drawing Sheets

OTHER PUBLICATIONS

Livak etal, "Oligonucleotides with Fluorescent Dyes at Opposite Ends Provide a Quenched Probe System Useful for Detecting PCR Product and Nucleic Acid Hybrifization", *PCR Methods and Appl;ications*, Cold Harbor Laboratory Press, pp 357–362, 1995.

Haronian, Dan, "In–Plane Degree of Freedom Optical Waveguide Displacement Sensors Based on Geometrical Modulation", *Sensors and Actuators*, Article 1950, 1998.

Haronian, Dan, "Suspended Optical Waveguide with In–Plane Degree of Freedom For Microelectricomechanical Applications", *Electronics Lett.*, 7(34): 663 et seq, 1998.

Gershoni et al, Protein Blotting in Uniform or Gradient Electric Fields, *Anal. Biochem.*, 144:32–40(1985).

O'Donnell et al "High–Density, Covalent Attachment of DNA to Silicon Wafers or Analysis by MALDI–TOF Mass Spectrometry"–Anal.Chem. 1997,69, pp 2438–2443.

Chrisey et al "Covalent attachment of synthetic DNA to self–assembled monolayer films" Nucleic Acids Research, 1996, vol. 24, No. 15 pp 3031–3039.

Adessi et al "Solid phase DNA amplification: characterization of primer attachment and amplification methanisms" Nucleic Acids Research, 2000, vol. 28, No. 20 e87.

Weissman et al "Modes of periodically Segmented Waveguides" Journal of Lightwave Technology vol. 11, No. 11 Nov. 1993.

Weissman "Evanescent field sensors with periodically segmented waveguides" Applied Optics vol. 36, No. 6, Feb. 20, 1997.

Weissman et al "Periodically Segmented Waveguides" Guided Wave Optoelectronics 1995 pp 313–320.

Weissman et al. "Periodically Segmented Waveguides" Trends in Lightwave Tech, Jan. 1994 pp 61–72.

Cheng et al, "Cip PCR.II. Investigation of Different PCR Amplification Syatems in Microfabricated Silicon–Glass Chips", *Nucleic Acid Research*, 24(2): 380–385, 1996.

"Product Development Worldwide", http//www.pagebleu.com/sratcom/levell/prods.htm: see–Affymetrix, Quidel Corp., Nanogen and Mosaic Tehnologies.

Gourley et al, "Surface Emitting Semiconductor Laser Spectroscopy/Microscopy for Rapid Probing of Blood Cells", http//epswww.

Boiarski et al, "Integrated–Optic Sensor with Macro–Flow Cell", *SPIE*, vol. 1793, 199–211–, 1992.

"Optical Electronics", Amnon Yariv, *Saunders College Pub.*, pp 492–503.

Mann et al, "Chip PCR.I Surface Passivation of Microfabricated Silicon–Glass Chips for PCR", *Nucleic Acid Research*, 24(2):375–379, 1996.

Burns et al, "Microfabricated Structures for Integrated DNA Analysis", *Proc Natl. Assoc. USA*, 93:5556–5561, 1996.

Lamture et al, "Direct Detection of Nucleic Acid Hybridization on the Surface of a Charge Coupled Device", *Nucleic Acid Research*, 22(11):2131–2125, 1994.

Stutius et al, "Silicon Nitride Films on Silicon for Optical Waveguides", *Appl. Optics*, 16(12):32318–3222, 1977.

Mullah et al, "Efficient Synthesis of Double Dye–labeled Oligoeoxyribonucleotide Probes and their Application in Real Time PCR Assay", *Nucleic Acid Research*, 26(4): 1026–1031, 1998.

* cited by examiner

1D arrays of SiO$_2$ coated micro-cavities

SEQUENCE LISTING

<160> NUMBER OF SEQ ID NOS: 3

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence:primer
    42-mer oligonucleotide to be immobilized on chip

<400> SEQUENCE: 1
aatgcttaag ccatggcata tgaattaacc ctcactaaag gg                42

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence:
    oligonucleotide used to demonstrate presence of immobilized 42-mer
    primer (SEQ ID NO:1) on chip

<400> SEQUENCE: 2
ccctttagtg agggtt                                            16

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
    oligonucleotide used as downstream soluble primer for PCR using
    immobilized 42-mer (SEQ ID NO:1) as upstream primer

<400> SEQUENCE: 3
gtaatacgac tcactatagg gc                                     22

METHOD, CHIP, DEVICE AND SYSTEM FOR EFFECTING AND MONITORING NUCLEIC ACID ACCUMULATION

This is a continuation of U.S. patent application 09/157,531, filed Sep. 21, 1998, now abandoned.

FIELD AND BACKGROUND OF THE INVENTION

The present invention relates to the art of effecting and monitoring nucleic acid accumulation. More particularly, the present invention relates to a microfabricated chip including a waveguide formed with an optical microcavity in which nucleic acid accumulation can take place, which can be used to monitor nucleic acid accumulation. The invention further relates to a device constructed for accepting the chip and for effecting the monitoring of nucleic acid accumulation in the cavity therein. Yet, the invention further relates to a system which includes the chip and the device and to a method for effecting and monitoring nucleic acid accumulation using same.

Nucleic acid amplification methods, such as polymerase chain reaction (PCR), ligase chain reaction (LCR), nucleic acid sequence based amplification (NASBA) and related techniques have become a central technology in genetic engineering and molecular biology. These methods enable the detection of single copy genes and/or DNA fragments with a very high degree of sensitivity, due to the extreme amplification of the signal obtained. As a result, these methods are gradually becoming critical methods in genetic diagnostics as well.

Yet, while implemented, nucleic acid amplification methods call for a series of steps which are tedious, time consuming and require highly trained personnel in order to be effectively executed. It is, therefore, not surprising that efforts are undertook to streamline nucleic acid amplification methods by rendering such methods more amenable to automation.

Should nucleic acid amplification technology become rapid, easy to perform and simple and sensitive to readout results, then it would immediately be applicable to the enormous, world-wide practice of genetic diagnostics.

Immobilized DNA has been known for years and is routinely used in nucleic acid blotting technology. Immobilization of short oligonucleotides has also been demonstrated and standartized. Recent technologies have demonstrated the immobilization of oligonucleotides to micro fabricated chips, to provide templates for hybridization and new techniques for mass sequencing on DNA chips. Thus, the concept and chemistries of using immobilized oligonucleotides is not new.

The combination of DNA amplification and micro fabricated chip technology is also not new. Here the basic concept has been to exploit the attributes of conducting the PCR reaction in microchambers, therefore benefiting from very small volumes of reagents to be used. This obviously has advantages when sample is rare. See, for example, Shoffner et al. (1996), "Chip PCR I. Surface passivation of microfabricated silicon-glass chip for PCR", Nucleic Acids Research. Vol. 24, No. 2, 375–379; and Burns et al. (1996), "Microfabricated structures for integrated DNA analysis", Proc. Natl. Acad. Sci. USA, Vol. 93, 5556–5561.

U.S. Pat. No. 5,498,392, for example, discloses devices for amplifying a preselected polynucleotide in a sample by conducting a polynucleotide polymerization reaction. The devices comprise a substrate microfabricated to define a sample inlet port and a mesoscale flow system, which extends from the inlet port. The mesoscale flow system includes a polynucleotide polymerization reaction chamber in fluid communication with the inlet port which is provided with reagents required for polymerization and amplification of a preselected polynucleotide. In one embodiment the devices may be utilized to implement a polymerase chain reaction (PCR) in the reaction chamber (PCR chamber). The PCR chamber is provided with the sample polynucleotide, polymerase, nucleoside-triphosphates, primers and other reagents required for the polymerase chain reaction, and the device is provided with means for thermally controlling the temperature of the contents of the reaction chamber at a temperature controlled to dehybridize double stranded polynucleotide, to anneal the primers, and to polymerize and amplify the polynucleotide.

However, devices such as the device described in U.S. Pat. No. 5,498,392, although capable of supporting miniaturized amplification reactions, fail in providing monitoring means for monitoring such reactions in an automatable fashion, preferably in real-time.

There is thus a widely recognized need for, and it would be highly advantageous to have miniaturized chip, device, system and method for effecting and monitoring nucleic acid accumulation.

SUMMARY OF THE INVENTION

It is an object of the present invention to provide chip, device, system and method for effecting nucleic acid accumulation and monitoring thereof, preferably in real-time.

It is another object of the present invention to provide chip, device system and method for effecting nucleic acid accumulation via amplification and/or hybridization and monitoring thereof, preferably in real-time.

It is yet another object of the present invention to provide chip, device, system and method for effecting nucleic acid accumulation via polymerase or ligase chain reaction and monitoring thereof, preferably in real-time.

Thus, according to one aspect of the present invention there is provided a nucleic acid accumulation analyzing chip comprising an optical waveguide having a radiation input port and a radiation output port, the optical waveguide being formed with at least one optical microcavity along its optical path, at least one oligonucleotide being immobilized to the optical waveguide in the microcavity, such that when the at least one oligonucleotide is contacted with reaction reagents under conditions allowing a nucleic acid accumulation reaction to take place, accumulated nucleic acid is detectable by providing radiation at the radiation input port of the optical waveguide and monitoring radiation signal modulation at the radiation output port of the optical waveguide.

According to another aspect of the present invention there is provided a nucleic acid accumulation analyzing system comprising (a) a nucleic acid accumulation analyzing chip including an optical waveguide having a radiation input port and a radiation output port, the optical waveguide being formed with at least one optical microcavity along its optical path, at least one oligonucleotide being immobilized to the optical waveguide in the microcavity; (b) a radiation source being in optical communication with the radiation input port; and (c) a radiation detector being in optical communication with the radiation output port; such that when the at least one oligonucleotide is contacted with reaction reagents under conditions allowing a nucleic acid accumulation reaction to take place, accumulated nucleic acid is detectable by providing radiation at the radiation input port of the optical waveguide via the radiation source and monitoring radiation signal modulation at the radiation output port of the optical waveguide via the radiation detector.

According to yet another aspect of the present invention there is provided a nucleic acid accumulation analyzing device comprising (a) a housing being formed with an acceptor for accepting a nucleic acid accumulation analyzing chip including an optical waveguide having a radiation input port and a radiation output port, the optical waveguide being formed with at least one optical microcavity along its optical path, and at least one oligonucleotide being immobilized to the optical waveguide in the microcavity; (b) a radiation source being engaged by the housing, the radiation source being in optical communication with the radiation input port of the nucleic acid accumulation analyzing chip when engaged in the acceptor; and (c) a radiation detector being engaged by the housing, the radiation detector being in optical communication with the radiation output port of the nucleic acid accumulation analyzing chip when engaged in the acceptor; such that when the at least one oligonucleotide is contacted with reaction reagents under conditions allowing a nucleic acid accumulation reaction to take place, accumulated nucleic acid is detectable by providing radiation at the radiation input port of the optical waveguide via the radiation source and monitoring radiation signal modulation at the radiation output port of the optical waveguide via the radiation detector.

According to still another aspect of the present invention there is provided a method of monitoring nucleic acid accumulation comprising the steps of (a) providing an optical waveguide being formed with an optical microcavity containing at least one oligonucleotide being immobilized thereat; (b) effecting nucleic acid accumulation by contacting the at least one oligonucleotide with reaction reagents under conditions allowing a nucleic acid accumulation reaction to take place; and (c) monitoring nucleic acid accumulation by passing radiation through the optical microcavity and monitoring a signal modulation of the radiation, associated with nucleic acid accumulation.

According to further features in preferred embodiments of the invention described below, the optical waveguide is of $Si_3N_4$.

According to still further features in the described preferred embodiments a support layer is provided supporting the optical waveguide.

According to still further features in the described preferred embodiments the optical microcavity splits the waveguide, such that a bottom of the optical microcavity is effected by the support layer.

According to still further features in the described preferred embodiments the support layer is of $SiO_2$.

According to still further features in the described preferred embodiments a foundation layer is provided for supporting the support layer.

According to still further features in the described preferred embodiments the foundation layer is of doped silicon and serves as a resistor layer being in heat transfer relation with the optical microcavity. The resistor layer serves for providing the optical microcavity with heat for generating the conditions allowing the nucleic acid accumulation reaction to take place.

According to still further features in the described preferred embodiments a base layer is provided for supporting the foundation layer.

According to still further features in the described preferred embodiments the base layer is of silicon.

According to still further features in the described preferred embodiments the optical microcavity has a volume in a range of about 1 to about 10 cubic micrometers.

According to still further features in the described preferred embodiments the at least one oligonucleotide is immobilized in the optical microcavity in a surface density of between about $10^3$ oligonucleotide molecules per square micrometer and about $10^6$ oligonucleotide molecules per square micrometer.

According to still further features in the described preferred embodiments the nucleic acid accumulation reaction is selected from the group consisting of polymerase chain reaction, ligase chain reaction, nucleic acid sequence based amplification and nucleic acid hybridization.

According to still further features in the described preferred embodiments the radiation source provides a coherent radiation.

According to still further features in the described preferred embodiments the radiation source provides radiation in the visible range.

According to still further features in the described preferred embodiments the radiation source includes a laser source.

According to still further features in the described preferred embodiments the radiation detector serves for detecting radiation intensity modulation associated with nucleic acid accumulation.

According to still further features in the described preferred embodiments the radiation detector serves for detecting radiation phase modulation associated with nucleic acid accumulation.

According to still further features in the described preferred embodiments the radiation source and the a radiation detector are engaged in a nucleic acid accumulation analyzing device, the device is formed with an acceptor for receiving the nucleic acid accumulation analyzing chip.

The present invention successfully addresses the shortcomings of the presently known configurations by providing chip, device, system and method for effecting nucleic acid accumulation and monitoring thereof in real-time and in a fully automated fashion.

BRIEF DESCRIPTION OF THE DRAWINGS

The invention herein described, by way of example only, with reference to the accompanying drawings, wherein.

DESCRIPTION OF THE PREFERRED EMBODIMENTS

The present invention is of a chip including a waveguide formed with an optical microcavity in which nucleic acid accumulation can take place, which can be used for monitoring nucleic acid accumulation therein, preferably in real-time. The invention is further of a device constructed for accepting the chip and for effecting the monitoring of nucleic acid accumulation in the optical microcavity therein. The invention is further of a system which includes the chip and the device and of a method for effecting and monitoring nucleic acid accumulation using same. Specifically, the present invention can be used to effect and simultaneously monitor the accumulation of nucleic acid products of polymerase and ligase chain reactions.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
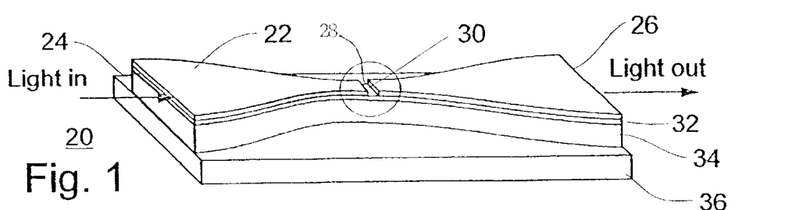
FIG. 1 is a schematic perspective depiction of a nucleic acid accumulation analyzing chip according to the present invention.
Figure 2:
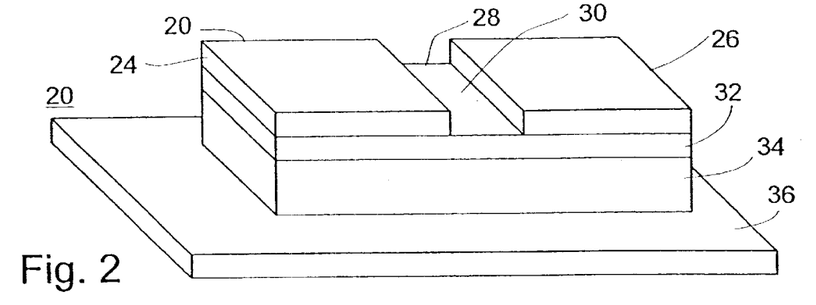
FIG. 2 is an enlargement of the circled region in FIG. 1, showing in greater detail the optical microcavity region of the nucleic acid accumulation analyzing chip according to the present invention.

Referring now to the drawings, FIGS. 1–2 schematically illustrate the nucleic acid accumulation analyzing chip according to the present invention, which is referred to hereinbelow as chip 20.

Chip 20 includes an optical waveguide 22. Optical waveguide 22 has a radiation input port 24 and a radiation output port 26. Waveguide 22 is formed with at least one optical microcavity 28 along its optical path. According to a preferred embodiment of the present invention optical microcavity 28 has a volume in a range of about 1 to about 10 cubic micrometers. According to the present invention, at least one oligonucleotide is immobilized (e.g., covalently linked) to at least one face 30 of microcavity 28, such that when the oligonucleotide is contacted with reaction reagents under conditions allowing a nucleic acid accumulation reaction to take place, accumulated nucleic acid is detectable by providing radiation at radiation input port 24 of optical waveguide 22 and monitoring radiation signal modulation at radiation output 26 port of optical waveguide 22.

The nucleic acid accumulation reaction according to the present invention can be any reaction that results in nucleic acids adhering to the immobilized oligonucleotide present in microcavity 28.

Methods of immobilizing oligonucleotides to a solid support and of using these oligonucleotides to support nucleic acid hybridization and/or amplification via a polymerase chain reaction are well known in the art. See, for example, U.S. Pat. No. 5,641,658 to Adams et al., which is incorporated by reference as if fully set forth herein.

The reaction can, for example, be a polymerase chain reaction, in which template dependent exponential amplification of a template is effected by contacting the immobilized oligonucleotides with a second (e.g., free) oligonucleotide, such that each of the oligonucleotides is capable of base pairing with opposing strands of the template and further such that the 3' ends of the oligonucleotides when so annealed to the template face each other; nucleoside-triphosphates; suitable buffer; and a nucleic acid polymerase enzyme (preferably a heat stable enzyme); and cycling the temperature of microcavity 28 among denaturation temperature (e.g., about 94° C.) for effecting denaturation of annealed nucleic acids present in microcavity 28, annealing temperature (e.g., typically in a range of 45–65 ° C.) for effecting template dependent annealing of templates to the oligonucleotides; and elongation temperature (e.g., 72° C.) for effecting enzyme dependent elongation of the oligonucleotides in a template dependent manner. In another embodiment both oligonucleotides are immobilized.

Alternatively, the reaction can, for example, be a ligase chain reaction, in which template dependent amplification of oligonucleotide ligation product is effected by contacting the immobilized oligonucleotide with a second free oligonucleotide, such that each of the oligonucleotides is capable of base pairing with a strands of the template and further such that the 3' end of one of the oligonucleotides and the 5' end of the other oligonucleotide when so annealed to the template juxtapose each other; adenosine-triphosphate (ATP); suitable buffer; and a ligase enzyme (preferably a heat stable enzyme); and cycling the temperature of microcavity 28 among denaturation temperature (e.g., about 94° C.), for effecting denaturation of annealed nucleic acids in microcavity 28, annealing temperature (e.g., typically in a range of 45–65° C.), for effecting template dependent annealing of templates to the oligonucleotides; and ligation temperature (e.g., 72° C.), for effecting enzyme dependent ligation of the oligonucleotides in a template dependent manner.

Still alternatively the reaction can, for example, be a hybridization reaction, in which template dependent hybridization is effected between the oligonucleotide immobilized within microcavity 28 and a free nucleic acid template under appropriate hybridization conditions (e.g., salt concentration, temperature).

The template according to the present invention can be present in a purified or crude nucleic acid preparation. For that matter, the template can be included in whole cells, e.g., white blood cells or bacterial cells. It can also be in a form of a body fluid or tissue including such cells, or alternatively viruses. Release of the template from the cells or viruses is efficiently effected under heat, e.g., the denaturation temperature employed in the polymerase and ligase chain reactions described hereinabove.

In any case, according to a preferred embodiment of the present invention the oligonucleotide is immobilized in optical microcavity 28 in a surface density of between about $10^3$ oligonucleotide molecules per square micrometer and about $10^6$ oligonucleotide molecules per square micrometer.

See, Lamture J. B. et al. (1994), Nucleic Acids Research, 22:2121–2125; and O'Donnell, M. J. et al. (1997), Anal. Chem., 69:2438–2443.

As further detailed hereinunder, in any one of these cases, nucleic acid accumulation is monitored according to the present invention either in real-time and/or shortly after the termination of the nucleic acid accumulation reaction, by providing radiation at radiation input port 24 of optical waveguide 22 and monitoring radiation signal modulation at radiation output 26 port of optical waveguide 22.

According to a preferred embodiment of the present invention, optical waveguide 22 is of $Si_3N_4$, which over short distances (e.g., up to 1 mm) is effective in passing light from 400 nm to 900 nm, with losses of no more then 3 db/mm for wavelengths around 400 nm, with losses of no more then 1 db/mm for wavelengths around 550 nm, and with losses of no more then 20 db/mm for wavelengths around 900 nm. In wavelengths between about 600 nm and about 900 nm, $Si_3N_4$ waveguides losses over such distances is small (e.g., 0.5–10 db). To this effect, the reader is referred to Studius W. and W. Streifer (1977), "Silicon nitride films on silicon for optical waveguides", Applied Optics, Vol. 16., No. 12., pp. 3218–3222; and to Dan Haronian (1998), Electronics Letters, Vol. 7, No. 34, pp. 663–664. It will be appreciated that the distances to which light is expected to travel within the waveguide according to the present invention are very short and therefore, radiation outside the above spectral ranges can also be used, even id losses become higher.

According to a preferred embodiment of the present invention, nucleic acid accumulation analyzing chip 20 further includes a support layer 32. Layer 32 serves to support optical waveguide 22. In one embodiment of the invention, optical microcavity 28 splits waveguide 22, such that a bottom face 30 of optical microcavity 28 is effected by support layer 32. Support layer 32 is preferably made of $SiO_2$, a substance which was used in the past to immobilize oligonucleotides thereto. For example, U.S. Pat. No. 5,641, 658 to Adams et al., which is incorporated by reference as if fully set forth herein, teaches the immobilization of oligonucleotides to $SiO_2$ surfaces.

According to another preferred embodiment of the present invention, nucleic acid accumulation analyzing chip 20 further includes a foundation layer 34. Foundation layer 34 serves for supporting support layer 32 and it is preferably made of doped silicon (doped Si). As such, it can serve as a resistor layer deployed in heat transfer relation with optical microcavity 28 for providing optical microcavity 28 with heat for generating conditions allowing a nucleic acid accumulation reaction, as for example described above, to take place. Foundation layer can also be made of metal of high resistivity, such as, but not limited to, chromium, titanium-tungsten, tungsten, to otherwise similarly function.

Since for most applications the heat required to support nucleic acid accumulation is above room temperature, and due to the miniaturized construction of chip 20 and the fast heat transfer associated therewith, the need for active cooling means is obviated. Yet, in other cases cooling means can be effective and therefore included. Such cooling means can be effected, for example, by a mechanism effective in cooling the atmosphere surrounding chip 20. Alternatively, it can be effected by the Peltier effect.

According to another preferred embodiment of the present invention, nucleic acid accumulation analyzing chip 20 further includes a base layer 36. Base layer 36 serves for supporting foundation layer 34. Base layer 36 is preferably made of silicon (Si) or glass. Other substances are also applicable.

The production of $Si_3N_4$ waveguides featuring the additional layers as described hereinabove is described in detail, for example, in a paper entitled "In-plane degree of freedom optical waveguide displacement sensors based on geometrical modulation", by Dan Haronian, published in 1998, in Sensors and Actuators A, 69:217–225, and in a paper entitled "Suspended optical waveguide with in-plane degree of freedom for microelectromechanical applications", by Dan Haronian, published in 1998, in Electronics letters, Vol. 7, No. 34, 663–664, both are incorporated by reference as if fully set forth herein. These papers teach suspended optical waveguide displacement sensors (SOWDS) technology. The sensors are based on optical modulation in the form of energy losses and mode conversions, resulting from relative displacement of aligned and suspended waveguides. The building block of the suspended waveguides described is a single-crystal silicon (SCS) beam with the top layers thereof comprising of 0.6 $\mu$m thick $SiO_2$, 0.4 $\mu$m thick $Si_3N_4$, and 0.6 $\mu$m thick $SiO_2$. Additional silicon layers, e.g., doped silicon can be added. The SCS has a typical cross section of 1.6 $\mu$m×10 $\mu$m and may guide light with wavelength in the 1.3–1.5 $\mu$m range. The first $SiO_2$ layer serves as a buffer layer that allows light with wavelength in the range 0.6–0.9 $\mu$m to be guided in the $Si_3N_4$ layer with substantially no light losses over short distances. The paper discusses the theoretical considerations, the fabrication process, and the characterizations of fixed-free and fixed-fixed SOWDS configurations. The same layer tacking formed with additional microcavities formed in the $Si_3N_4$ layer is used according to the present invention, as further detailed below and exemplified in FIGS. 7–8.

Figure 3:
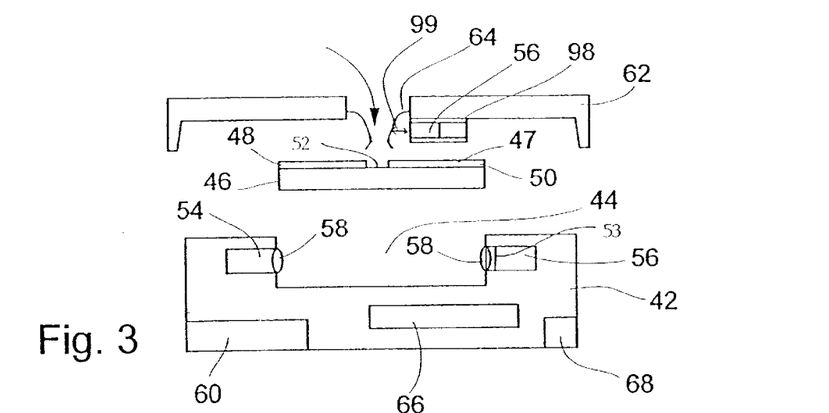
FIG. 3 is a schematic cross sectional depiction of a nucleic acid accumulation analyzing device and system according to the present invention.

Referring now to FIG. 3, according to another aspect of the present invention there is provided a nucleic acid accumulation analyzing device, which is referred to hereinbelow as device 40. It will be appreciated that FIG. 3 is drawn out of scale and out of internal proportions.

Device 40 includes a housing 42 formed with an acceptor 44. Acceptor 44 is designed for accepting a nucleic acid accumulation analyzing chip 46. Chip 46 includes an optical waveguide 47 having a radiation input port 48 and a radiation output port 50. Waveguide 47 is formed with at least one optical microcavity 52 along its optical path. At least one oligonucleotide is immobilized onto optical waveguide 47 in microcavity 52. Additional features of chip 46 are described hereinabove with respect to chip 20.

Device 40 further includes a radiation source 54. Source 54 is engaged by housing 42 and is in optical communication with radiation input port 48 of nucleic acid accumulation analyzing chip 46 when the latter is engaged by acceptor 44. Source 54 is preferably a coherent, e.g., laser source, yet non-coherent light sources are also applicable.

Device 40 further includes a radiation detector 56. Detector 56 is engaged by housing 42 and is in optical communication with radiation output port 50 of nucleic acid accumulation analyzing chip 46 when the latter is engaged by acceptor 44.

Device 40 preferably includes optical arrangements 58, which, for example, includes optic fiber(s), lenses, reflectors, beam splitters and the like, for directing radiation from source 45 via port 48, through waveguide 47 and microcavity 52, via port 50 to detector 56.

The construction of device 40 and chip 44 are selected such that when the oligonucleotide(s) immobilized within microcavity 52 is contacted with reaction reagents under conditions allowing a nucleic acid accumulation reaction to take place, accumulated nucleic acid is detectable by providing radiation at radiation input port 48 of optical waveguide 47 via radiation source 54 and monitoring radiation signal modulation at radiation output port 50 of optical waveguide 47 via radiation detector 56.

According to a preferred embodiment of the present invention, radiation source 54 provides coherent radiation, in the visible, ultraviolet or infrared ranges. According to a preferred embodiment detector 56 is a photodiode, yet it can also be a spectrophotometer or include a radiation sensitive article such as, but not limited to, a CCD. Detector 56 is selected to match the specification of the radiation provided by source 50. Radiation detectors suitable for monitoring light modulation (e.g., intensity, attenuation, phase modulation, etc.) in the above specified spectral ranges are well known in the art. For example, the InGaAs PIN Photodetector model 2011 from New Focus, Inc. (pg. 62, 1997/98 catalog, Vol. 8, http://www.newfocus.com). However, the radiation provided by source 54 should also match the capabilities of waveguide 47 to pass that radiation therethrough and through microcavity 52 onto detector 56. As already stated above, over short distances $Si_3N_4$ waveguides are effective in passing light from less than 400 nm to more than 900 nm, with low losses (up to 20 db). Outside this spectral range higher losses are experienced, yet functionality for the present application is not hampered due to the short distances involved.

Yet, the radiation provided by source 54 should also match the physical nature of the reaction of nucleic acid accumulation performed in microcavity 52, such that radiation modulation will take place in case of accumulation of nucleic acids therein.

Nucleic acids efficiently absorb light in the ultraviolet range, with absorption that peaks at about 260 nm. Thus, if source 54 is selected to emit light in the ultraviolet range, accumulation of nucleic acids in microcavity 52 can readily be detected by a suitable detector sensitive to radiation in this spectral range, because as the concentration of immobilized accumulated nucleic acid increases within microcavity 52, more radiation will be absorbed and less radiation will therefore be detected by detector 56.

A plurality of intercalating agents, such as ethidium bromide, propidium iodide, acridine orange and the like, are know to intercalate into double-stranded DNA molecules. As a result of such intercalation, these ligands undergo a change in their spectral properties, such as absorption and fluorescence, as further detailed hereinunder. Therefore, adding such ligands to the reaction according to the present invention will result in radiation attenuation and emission enhancement which can be detected by detector 56. Ethidium bromide, for example, has a main absorption (excitation) peak at 510 nm, yet ethidium dimers (homo- and heterodimers) can be excited at 488 nm (argon laser). Thiazolium and oxazolium nucleic acid stains (Molecular Probes Inc.), such as, Yo-Pro-1 and To-PRO-1 are optimally excited by the argon laser. To-PRO-3 is excited by the Hb-Ne laser at 633 nm. These dyes has fluorescence intensity of almost zero, except when they are intercalated in nucleic acids. Benzothiazolium-4-quinolinium dimer (TOTO-1) fluorescence increases about 3000-fold upon binding to DNA or RNA. It is virtually nonfluorescent unless bound to DNA or RNA. ẏYOYO-1 matches better the 488-nm line of the argon laser than TOTO-1. TOTO-3 can be excited by the He:Ne laser at 633 nm and the Kr laser at 647 nm. 9-Amino-6-Chloro-2-Methoxyacridine is a DNA intercalator which binds poly[d(A-T)] with Kd of approximately 100 nM. It is excited at 430 nm. Excitation thereof is possible with most light sources. Additional information concerning thiazolium and axazolium nucleic acid stains is provided in the Molecular Probes Inc. catalog.

Tagged, e.g., fluorescently tagged, nucleoside-triphosphates, free oligonucleotides or templates can be employed to tag the accumulated nucleic acids within microcavity 52. The tag has unique optical properties which cause radiation modulation which is detectable by detector 56. Suitable fluorescent tags include, but are not limited to, FITC, Spectrum Green or Cy2 (Amersham) efficiently absorbing radiation at 475–495 nm, Cy3 (Amersham) and Texas-Red, efficiently absorbing radiation at 540–570 nm, and Cy5 (Amersham), efficiently absorbing radiation at 630–670 nm. Oligonucleotides, templates, as well as nucleoside-triphosphates tagged with the above listed fluorophores are well known in the art. A combination of quenchers and fluorescent dyes can also be employed, in a fashion similar to as described, for example, in Lee et al. (1993), "Allelic discrimination by nick-translation PCR with fluorogenic probes", Nucleic Acids Research, Vol. 21, No. 16, pp. 3761–3766, or in Livak et al. (1995), "Oligonucleotides with fluorescent dyes at opposite ends provide a quenched probe system useful for detecting PCR products and nucleic acid hybridization", PCR methods and applications, Cold Spring Harbor Laboratory Press, pp. 357–362, both are incorporated by reference as if fully set forth herein. See also, Mullah et al. (1998), "Efficient synthesis of double dye-labeled oligodeoxyribonucleotide probes and their application in a real-time PCR assay" Nucleic Acids Research, Vol. 26, No. 4, pp. 1026–1031.

It will be appreciated that the emission peaks of the above described intercalators and tags fall within the visual range. Using a suitable filter 53 positioned between chip 46 and detector 56, one can monitor the accumulation of excitable fluorescence in microcavity 52 to thereby monitor nucleic acid accumulation therein. In this case source 54 provides radiation in the excitation wavelength, which radiation is substantially blocked by filter 53, whereas detector 56 is designed to detect radiation in the emission wavelength of the tag or intercalator employed. Alternatively, and preferably, detector 56 in this case is brought into position above microcavity 52 when cover 64 is covers chip 46, so as to be away from the excitation radiation which is directional in nature, to thereby sense substantially only emission radiation. One of ordinary skills in the art would know how to ensure such positioning of detector 56, e.g., by translatably engaging it onto cover 64 and providing a translation mechanism 98 for translating it into position when so required, as indicated by arrow 99.

According to another embodiment of the present invention tagged probes capable of hybridizing with the accumulated nucleic acids in case of amplification can be used post reaction for monitoring nucleic acid accumulation within microcavity 52.

The accumulation of nucleic acids in microcavity 52 has additional detectable optical effects. For example, it can lead to a change in the index of refraction of the solution within microcavity 52, a result of which is radiation modulation due to Fresnel losses.

Table 1 below describe the change in the index of refraction of Na-DNA with concentration of the nucleic acid dn/dc at several NaCl concentrations at 25° C.

TABLE 1

| [NaCl] mol-liter$^{-1}$ | 436 nm | dn/dc ml-gram$^{-1}$ 514.5 nm | 546 nm | 633 nm |
|---|---|---|---|---|
| 0 | 0.183 (0.186) | 0.180 | 0.176 0.179 | 0.175 |
| 0.005 | | 0.176 | | |
| 0.01 | | 0.176 | | |
| 0.05 | | 0.174 | | |
| 0.1 | | 0.171 | | |
| 0.2 | 0.174 | 0.168 | 0.165 | 0.164 |

Taken from Landolt-Bornstein "Numerical Data and Functional Relationships in Sciences and Technology", New Series. Ed. in chief: O. Madelung, Group VII: Biophysics, Volume 1, Nucleic Acids, Subvolume c., Spectroscopic and Kinetic Data Physical Data 1 (Springer Verlag), page 268–269.

Taking for an increase of 1 gram/ml a change in the refractive index, n, of 0.17, the expected change in n for the calculated increase in nucleotide residue concentration expected by performing PCR is as follows: Expected increase in concentration of nucleotide residue is 0.09 M, corresponding to a concentration increase of 29 mg/ml and an increase of refraction index of 0.09×324×0.17/1000= 0.005, which is a readily detectable magnitude. To this effect the reader is referred to Boiarski AA et al., 1992, "Integrated Optics and Microstrutures" SPIE Vol. 1793:199–211; Lin VSY et al., 1997, Science 278:840–843; and Schneider BH et al., 1997, Clin. Chem. 43:1757–1763.

Figure 5:
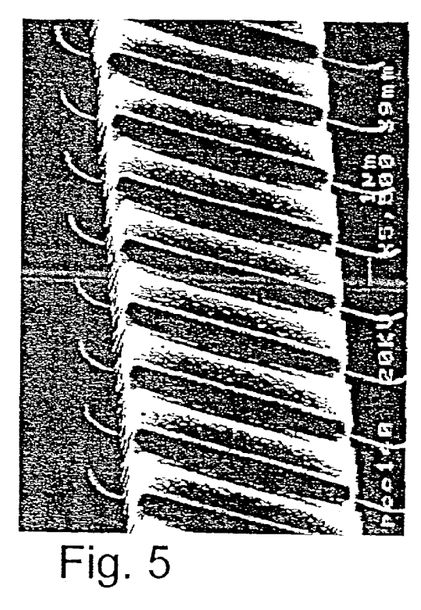
FIG. 5 is a scanning electron micrograph showing a nucleic acid accumulation analyzing chip according to the present invention including a waveguide formed with a plurality of optical microcavities.
Figure 6:
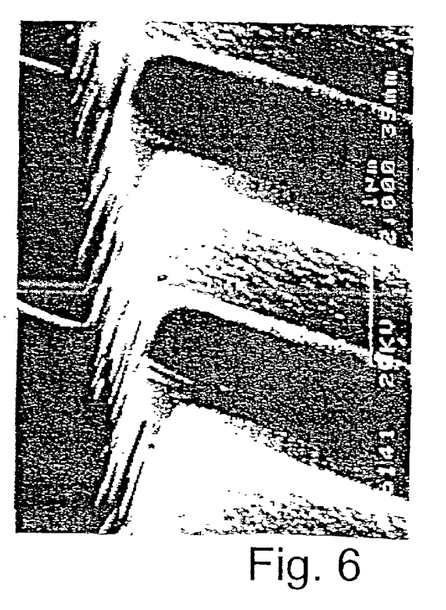
FIG. 6 is an enlargement of a portion of FIG. 5, showing in greater detail the optical microcavity region of the nucleic acid accumulation analyzing chip according to the present invention.

Similarly, a periodic waveguide which includes a plurality of periodic microcavities (see FIGS. 5–6) can be employed and serve as an optical filter which has different filtering capabilities depending on the index of refraction within the plurality of cavities, which itself depends on nucleic acid accumulation. The radiation is differently affected by the different filtering capabilities and therefore radiation modulation associated with nucleic acid accumulation is detectable by detector 56.

If enough organized, e.g., under the influence of an electric field or a unidirectional flow, the nucleic acids accumulated in microcavity 52 can form a lattice-like structure that diffracts and therefore modulates radiation of the appropriate wavelength.

A Mach-Zehnder effect can be obtained by aligning two waveguides as described, only in one of which nucleic acid accumulation takes place, whereas the other serves as a reference. A beam splitter is used to divide the radiation obtained from source 54 into two parts that are then launched into the two waveguides. The outputs meat at another beam splitter and the two resulting beams are then allowed to fall onto suitable photodetectors, thus a radiation phase change can be detected upon nucleic acid accumulation.

Structural studies on nucleic acids in solution have been carried out employing UV and IR absorption, circular dichroism (CD), laser Raman, fluorescence, light scattering and NMR techniques. For reviews, see Bloomfield, Va. et al. (1974), "Physical Chemistry of Nucleic Acids", Harper & Row, New York. As will be appreciated by one ordinarily skilled in the art, these methods and modifications thereof are also applicable for monitoring nucleic acid accumulation according to the present invention, because each of which is associated with radiation modulation as a function of nucleic acid concentration.

According to a preferred embodiment of the present invention, device 40 includes a power source 60. Power source 60 serves to power radiation source 54, detector 42 and chip 46, if so required, e.g., to heat resistor layer 34 (FIGS. 1–2). Source 60 is preferably a battery, e.g., lithium battery. Yet source 60 can also be net electricity.

According to another preferred embodiment of the invention, device 40 further includes a cover 62. Cover 62 is used to shield detector 56 from external radiation effects. Cover 62 is preferably formed with a funnel 64. Funnel 64 is positioned such that it faces microcavity 52 when chip 46 is within acceptor 44 and cover 62 is closed. Funnel 64 serves to load microcavity 52 with a reaction mixture for enabling nucleic acid accumulation. Funnel 64 further serves to hold a reservoir of the mixture, from which reservoir building blocks for nucleic acid accumulation are derived. The reservoir is typically in several orders of magnitude larger than the volume of microcavity 52, such that it is never depleted and it enables efficient accumulation of nucleic acids within microcavity 52. Funnel 64 can also serve to remove, e.g., by washing, the remaining of the reaction mixture from microcavity 52, leaving therein only the immobilized accumulated nucleic acids. It can also serve to introduce ligands into microcavity 52 following the end of the accumulation reaction, such as chelating or tagged probes.

Application of a liquid into microcavity 52 can be greatly benefited by placing device 40 in a vacuum chamber, such that air is no longer trapped within microcavity 52. Alternatively, device 40 can be dipped in the appropriate liquid which will then fill microcavity 52. The latter is exemplified in Example 3 hereinunder. The liquid includes all the reagents for propagating and/or monitoring the nucleic acid accumulation reaction as further detailed herein.

As already mentioned above, device 40 can be used for real-time monitoring of nucleic acid accumulation in microcavity 52. Alternatively, accumulation can be determined after the termination of the accumulation reaction. These features of the present invention depend to a large extent on the strategy employed for detecting nucleic acid accumulation. In most cases, however, real-time monitoring is readily effected.

In any case, device 40 preferably includes a display 66 and a chip-on-board 68, for analyzing and displaying data related to the accumulation of nucleic acids within microcavity 52 as measured by detector 56, as further detailed hereinunder.

The configuration described hereinabove is designed as a partially disposable configuration. While chip 46 and cover 62 which are contacted with nucleic acids derived from a patient are disposable, device 40 itself is reusable.

Yet fully disposable systems are also within the scope of the present invention. Such systems include nucleic acid accumulation analyzing chip 46, radiation source 54, and radiation detector 56, permanently arranged essentially as described above and disposable after use.

According to another aspect of the present invention there is provided a method of monitoring nucleic acid accumulation. The method is effected by executing the following method steps, in which in a first step an optical waveguide formed with an optical microcavity containing at least one oligonucleotide immobilized thereat is provided. In a second step of the method nucleic acid accumulation is effected by contacting the oligonucleotide with reaction reagents under conditions allowing a nucleic acid accumulation reaction to take place. While in a third step of the method nucleic acid accumulation is monitored by passing radiation through the waveguide and the optical microcavity therein and monitoring a signal modulation of the radiation which is associated with nucleic acid accumulation.

Figure 9:
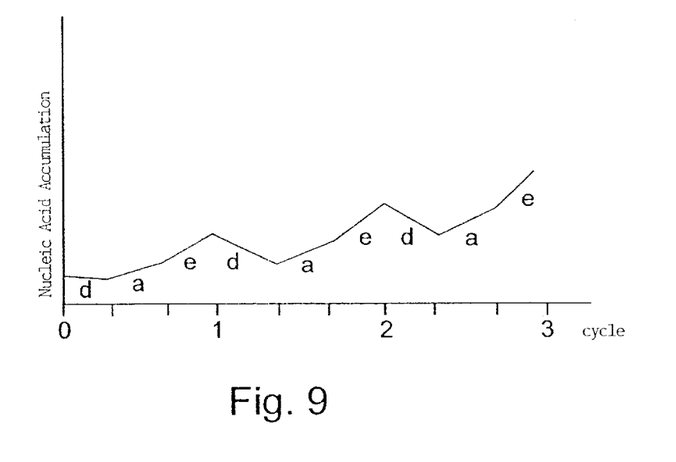
FIG. 9 is a plot demonstrating a pattern of nucleic acid accumulation during a polymerase chain reaction performed and monitored according to the method of the present invention.

With reference now to FIG. 9, presented is a plot showing a pattern of nucleic acid accumulation according to the present invention, as monitored in real-time for a polymerase chain reaction involving a single immobilized oligonucleotide. During denaturations (d) the amount of nucleic acid in the optical microcavity decreases (except for the first denaturation) because double stranded nucleic acid molecules dissociate into immobilized and free strands, the free strands are free to join the reservoir which is external to the microcavity. During annealings (a) the amount of nucleic acid in the microcavity is increased as templates adhere primarily to the immobilized oligonucleotides. During elongations (e) the amount of nucleic acid in the microcavity is again increased as nucleoside-triphosphates are incorporated into growing nucleic acid strands.

The accumulation pattern presented in FIG. 9 is very unique and can be used as a reference set of data in an algorithm directed at determining whether PCR amplification takes place or not. Such an algorithm will retrieve data collected in real-time relating to actual accumulation of nucleic acids in the optical microcavity and will compare the data to a reference set of data, as described, for example, in FIG. 9, to thereby identify characteristic nucleic acid accumulation associated with polymerase chain reaction amplification. This algorithm can be executed by chip-on-board 68 (FIG. 3), which includes to this effect a memory module for storing the reference set of data and the measured data, and a computing module for comparing therebetween. The comparison results can be displayed in a suitable form on display 66.

Each of the various embodiments and aspects of the present invention as delineated hereinabove and as claimed in the claims section below finds experimental support in the Examples section that follows.

EXAMPLES

Reference is now made to the following examples, which together with the above descriptions, illustrate the invention in a non limiting fashion.

Example 1

Theoretical Considerations

The following concerns some calculations related to nucleic acid accumulation within the microcavity of the analyzing chip according to the present invention.

Assume that the bottom face of the optical microcavity is 10 square micrometers and that its volume is 5 cubic micrometers or $5 \cdot 10^{-15}$ liter. Further assume that the surface density of oligonucleotide is $10^5$ molecules per 10 square micrometers and that all of which are immobilized to the bottom face of the microcavity, then the volume concentration of the oligonucleotide is $10^5$ molecules per 5 cubic micrometers, or $3.0 \cdot 10^{-5}$ M.

Assume that the oligonucleotide is 42 residues long, then the concentration of nucleotides in the microcavity is $1.4 \cdot 10^{-3}$ M. Assume that the PCR product is 1500 base pairs long and that all of the oligonucleotide molecules present in the microcavity were extended and now appear as a part of double stranded 1500 base pairs long molecules, then, following PCR the concentration of residues in the microcavity is 0.1 M. The conventional concentration of nucleoside tri-phosphates employed in PCR is 400 microM or $1.6 \cdot 10^{-3}$ M. The initial concentration of residues in the microcavity is therefore $(1.4 \cdot 10^{-3} \times 2) + 1.6 \cdot 10^{-3} = 4.4 \cdot 10^{-3}$ M. Assuming no depletion of reagents (infinite reservoir, because in a small microcavity as described the amount of nucleoside-triphosphates is insufficient to support substantial amplification), the increase of residues within the microcavity following PCR is therefore $0.1 \text{ M}/4.4 \cdot 10^{-3} = 23$ fold.

Figure 4:
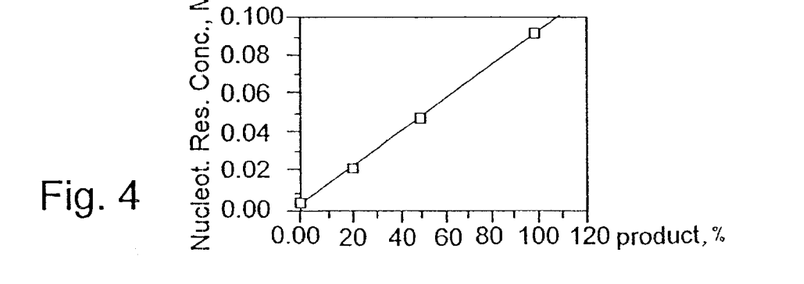
FIG. 4 is a plot showing the rise in concentration of nucleotide residues in the optical microcavity of the nucleic acid accumulation analyzing chip according to the present invention as a function of PCR product accumulation.

FIG. 4 describes the accumulation of nucleotide residues in the optical microcavity according to the present invention, which has been calculated as described above. Calculations were made for 20%, 50% and 100% yield of PCR product.

Assume that the height of the optical microcavity is 0.5 micrometers.

Knowing that the axial rise per nucleotide in DNA is 3.3 Angstrom or $3.3 \cdot 10^{-4}$ micrometers, the length of the DNA helixes formed is $3.3 \cdot 10^{-4} \cdot 1500 = 0.5$ micrometers. Thus, at 1500 base pairs the product is as long as the height of the microcavity.

Assume now that 5 mole % of the nucleoside-triphosphates employed are tagged with a fluorescent tag, i.e., the concentration of tagged nucleosides in the reservoir is $1.6 \cdot 10^{-3}/20 = 8 \cdot 10^{-5}$ M. This means that, on the average, for every 20 residues a tagged residue will be incorporated into the accumulated nucleic acid. The total concentration of tags after the reaction will rise as before 23 fold to $1.8 \cdot 10^{-3}$ M, forming a tremendous modulation on radiation.

Example 2

Waveguides

Figure 7:
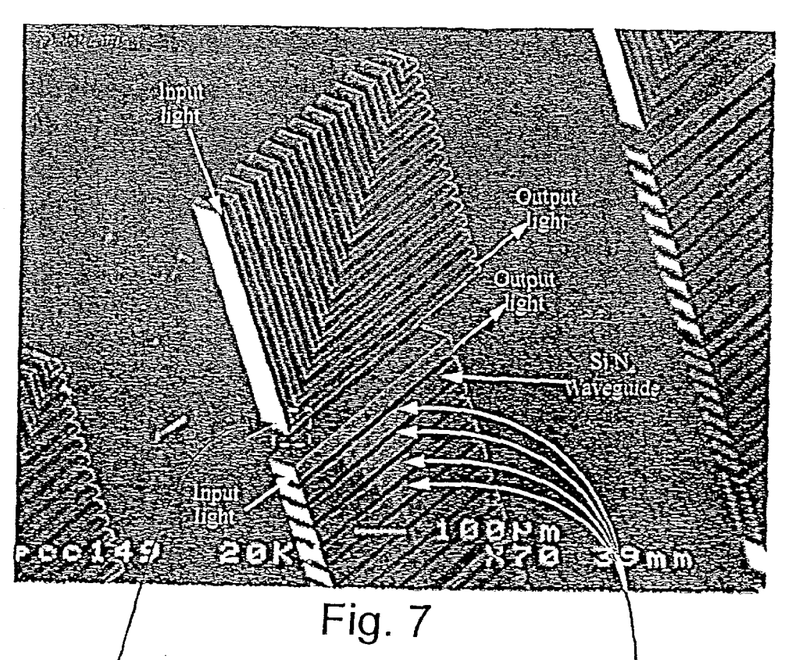
FIG. 7 is a scanning electron micrograph showing nucleic acid accumulation analyzing chips according to the present invention including linear and L shaped waveguides each formed with a single optical microcavity.
Figure 8:
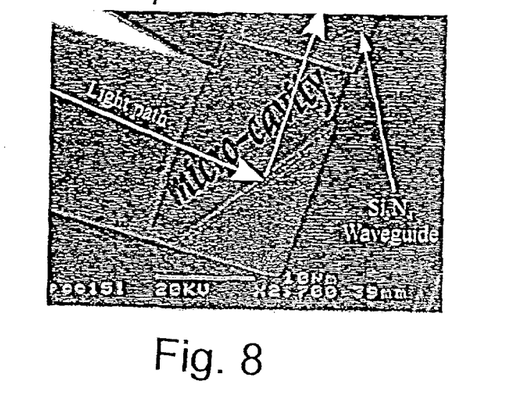
FIG. 8 is an enlargement of a square marked portion of FIG. 7, showing in greater detail an optical microcavity region of an L shaped waveguide according to the present invention.

FIGS. 5–8 show scanning electron micrographs of waveguides formed according to the present invention. The waveguide of FIGS. 5–6 include a plurality of cavities. The waveguides shown in FIGS. 7–8, each includes a single microcavity. The waveguides shown in the upper part of FIG. 7, each includes a microcavity designed to reflect light arriving thereat along an L-shaped optical path of the waveguide. An enlargement of that microcavity is shown in FIG. 8. The waveguides shown in the lower part of FIG. 7 are linear, each includes a $SiO_2$ coated microcavity of a variable length (lighter appearance).

These waveguides were manufactured in accordance with the teachings of Dan Haronian in "In-plane degree of freedom optical waveguide displacement sensors based on geometrical modulation", published in 1998 in Sensors and Actuators A, 69:217–225, and in "Suspended optical waveguide with in-plane degree of freedom for microelectromechanical applications", published in 1998 in Electronics Letters, Vol. 7, No. 34, 663–664, both are incorporated by reference as if fully set forth herein.

Example 3

PCR Reaction in a Microcavity of a Waveguide

Figure 10:
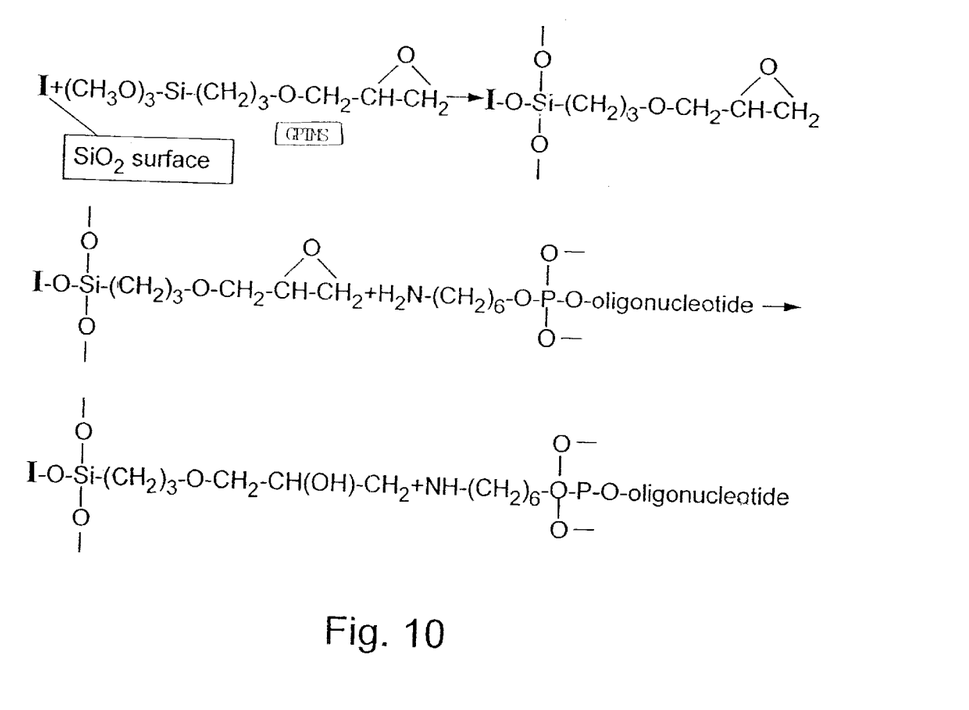
FIG. 10 present the chemical pathway employed for immobilizing an oligonucleotide in a microcavity formed in a chip according to the present invention.

Attachment of Oligonucleotide (5'-propylamine Modified 42-mer):

Epoxide Modification: The Silicon oxide surface of silicon chips was modified with gamma-glycidoxypropyl trimethoxy silane (GPTMS, see FIG. 10) as follows: Silicon oxide-coated silicon chips were washed in water and ethanol, passed twice through flame of a bunsen burner and checked for wetting of the surface by water. The chips were immersed in a solution of GPTMS in water (4%, pH 5.5–5.8) and heated at 90° C. for 30 minutes. The chips were water washed and used without delay.

Coupling of Primer Oligonucleotide to the Chip Surface: The oligonucleotide primer (42-mer, 5'-amino modified, $5'-H_2N-(CH_2)_6-PO_4^{2-}-$ AATGCTTAAGCCATGGCATATGAATTAACCCT CACTAAAGGG-3', SEQ ID NO: 1, 30 μM, 4 μl) in 0.5 M Na-carbonate was applied to the epoxide-modified chips (4×4 mm) placed in a humid closed chamber and kept at 40° C. overnight. Unreacted epoxide groups were capped by immersing the chips in a solution of thioglycerol (1% in 0.1 M Tris•HCL, pH 8.0) and incubating at 40° C. overnight. The chips were then water washed and stored in water at 4° C. until used.

For control experiments, epoxide-chips were treated with thioglycerol only.

Presence of the immobilized primer on the chip was demonstrated by applying 3' $^{32}$[P] radio labeled 42-mers to the epoxylated chip, under the above conditions.

Presence of immobilized primer on the chip surface was also demonstrated by hybridization of a 5' $^{32}$[P] radiolabeled oligonucleotide (16-mer, 5'-CCCTTTAGTGAGGGTT-3', SEQ ID NO: 2) consisting of a nucleotide sequence complementary to a stretch of 16 nucleotides of the immobilized 42-mer. The number of 42-mer molecules attached to chips were $10^{10-10^{11}}$ per square mm. Radioactivity of control chips treated only with thioglycerol was about 6% of the values measured for the chips containing the attached 42-mer.

Use of the Immobilized 42-mer as Primer in PCR: Chips (14–16 square mm) containing the immobilized 42-mer oligonucleotides which was designed to serve as an upstream PCR primer, were immersed in a solution (50 μl) containing a fragment nucleotides 625–791 of a pBluescript vector (STRATAGENE instructions manual to accompany the Lambda ZAP vectors Revision # 105001a, p. 42) as a template (about $10^{-12}$ M), Thermophilus aquaticus (Taq) DNA polymerase enzyme (2 units), a down stream soluble primer (22-mer 0.2 μM, 5'-GTAATACGACTCACTATAGGGC-3', SEQ ID NO: 3), and dNTPs (0.2 mM each with alpha-$^{32}$[P]-labeled dATP). The cycling program was one cycle at 95° C. for 5 minutes, followed by 30 cycles including 3 steps of 94° C. for 1 minute, 60° C. for 1 minute and 72° C. for 2 minutes, except for the last cycle wherein the reaction was kept at 72° C. for 7 minutes.

In a representative case the amount of bound DNA formed by PCR was calculated from the measured chip-radioactivity using a phosphoimager as $5 \times 10^9$ molecules per square mm ($8 \cdot 10^{-15}$ mols/square mm).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A nucleic acid accumulation analyzing chip comprising:
   i. an first optical waveguide having a radiation input port and a radiation output port;
   ii. at least one optical microcavity having a bottom face, said at least one optical microcavity placed in said first optical waveguide along its optical path; and
   iii. at least one oligonucleotide being immobilized to said bottom face of said optical microcavity, such that when said at least one oligonucleotide is contacted with reaction reagents under conditions allowing a nucleic acid accumulation reaction to take place, accumulated nucleic acid is detectable by providing radiation at said radiation input port of said optical waveguide and monitoring radiation signal modulation at said radiation output port of said first optical waveguide.

2. The nucleic acid accumulation analyzing chip of claim 1, wherein said first optical waveguide is of $Si_3N_4$.

3. The nucleic acid accumulation analyzing chip of claim 2, further comprising a support layer supporting said first optical waveguide, said support layer effecting said bottom face of said optical microcavity.

4. The nucleic acid accumulation analyzing chip of claim 3, wherein said support layer is of $SiO_2$.

5. The nucleic acid accumulation analyzing chip of claim 3, further comprising a foundation layer supporting said support layer, said foundation layer capable of serving as a resistor layer deployed in heat transfer relation with said optical microcavity, said resistor layer being for providing said optical microcavity with heat for generating said conditions allowing said nucleic acid accumulation reaction to take place.

6. The nucleic acid accumulation analyzing chip of claim 5, wherein said foundation layer includes a material selected from the group consisting of doped silicon, chromium, titanium-tungsten and tungsten.

7. The nucleic acid accumulation analyzing chip of claim 5, further comprising a base layer supporting said foundation layer.

8. The nucleic acid accumulation analyzing chip of claim 5, wherein said base layer includes a material selected from the group consisting of silicon and glass.

9. The nucleic acid accumulation analyzing chip of claim 1, wherein said optical microcavity has a volume in a range of about 1 to about 10 cubic micrometers.

10. The nucleic acid accumulation analyzing chip of claim 1, wherein said at least one oligonucleotide is immobilized to said bottom face of said optical microcavity in a surface density of between about $10^3$ oligonucleotide molecules per square micrometer and about $10^6$ oligonucleotide molecules per square micrometer.

11. The nucleic acid accumulation analyzing chip of claim 1, wherein said nucleic acid accumulation reaction is selected from the group consisting of polymerase chain reaction, ligase chain reaction, nucleic acid sequence based amplification and nucleic acid hybridization.

12. The nucleic acid accumulation analyzing chip of claim 1, further comprising a second optical waveguide aligned with said first optical waveguide in a Mach-Zender configuration, wherein said nucleic acid accumulation takes place only in said optical microcavity of said first optical waveguide, and wherein said second optical waveguide serves as reference.

* * * * *